(12) United States Patent
Bristow

(10) Patent No.: US 9,643,936 B1
(45) Date of Patent: May 9, 2017

(54) FORM OF TRIBENURON-METHYL, A PROCESS FOR ITS PREPARATION AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/955,147

(22) Filed: Dec. 1, 2015

(51) Int. Cl.
| | | |
|---|---|---|
| *A01N 47/36* | (2006.01) | |
| *A01N 25/12* | (2006.01) | |
| *A01N 25/14* | (2006.01) | |
| *C07D 251/16* | (2006.01) | |

(52) U.S. Cl.
CPC ......... *C07D 251/16* (2013.01); *A01N 47/36* (2013.01); *C07B 2200/13* (2013.01)

(58) Field of Classification Search
CPC .............................. A01N 47/36; C07D 251/16
See application file for complete search history.

(56) References Cited

U.S. PATENT DOCUMENTS

| | | | | |
|---|---|---|---|---|
| 4,954,628 A * | 9/1990 | Besenyei | ............. | C07D 521/00 544/197 |
| 5,550,238 A * | 8/1996 | Chiang | ................ | C07D 521/00 544/206 |
| 2015/0031877 A1* | 1/2015 | Hiratsuka | ............. | A01N 43/84 544/105 |

FOREIGN PATENT DOCUMENTS

EP 0202830 A1 11/1986

OTHER PUBLICATIONS

Roberts, R.M. et al. Modern Experimental Organic Chemistry. Holt, Rinehart and Winston, New York, 1979, pp. 49-58.*
HCAPLUS abstract 1999:261209 (1999).*
McClurg, R.B., "X-Ray Powder Diffraction (XRPD) to Describe Crystal Forms," Publication of SSCI an Aptuit Company, Jul. 9, 2008, pp. 1-23.*

* cited by examiner

*Primary Examiner* — John Pak
(74) *Attorney, Agent, or Firm* — Dickinson Wright PLLC

(57) ABSTRACT

A crystalline form of tribenuron-methyl of formula (I), the crystal preparation process, the analyses of the crystal through various analytical methods and using the crystal to prepare stable agrochemical formulation. The invention also describes the use of various solvents towards the crystalline form preparation conditions.

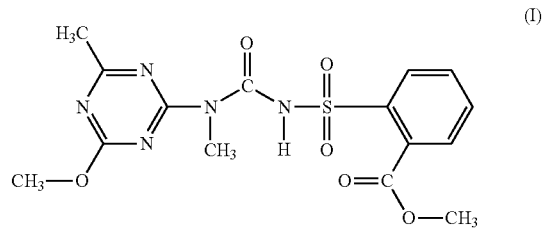

(I)

12 Claims, 4 Drawing Sheets

FORM OF TRIBENURON-METHYL, A PROCESS FOR ITS PREPARATION AND USE OF THE SAME

BACKGROUND

Field

The present disclosure relates to a crystalline form of (methyl 2-[4-methoxy-6-methyl-1,3,5-triazin-2-yl(methyl) carbamoylsulfamoyl]benzoate) (tribenuron-methyl), to its preparation processes and to its use in agrochemical preparations.

Description of Related Art

Tribenuron-methyl (methyl 2-[4-methoxy-6-methyl-1,3,5-triazin-2-yl(methyl)carbamoylsulfamoyl] benzoate) is a member of the sulfonylurea group of chemicals and used as herbicide. Tribenuron-methyl is a selective post-emergence sulfonylurea herbicide for the control of broadleaved weeds on crops, such as cereals and sunflower. Like other sulfonylureas, the mode of action is via inhibition of the enzyme acetolactate synthase (ALS), and thus prevention of the biosynthesis of the essential amino acids isoleucine and valine.

Tribenuron-methyl has molecular formula of $C_{15}H_{17}N_5O_6S$. Its chemical structure is

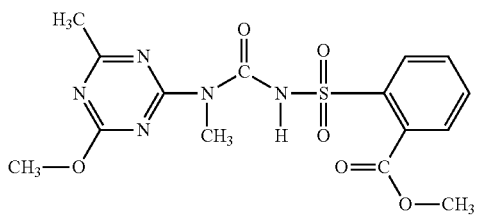

(I)

SUMMARY

The commercially available tribenuron-methyl, which is usually manufactured by the process described in EP 0202830, which is incorporated herein by reference for all purposes, is present in an amorphous state. It has been found that tribenuron-methyl in amorphous state is highly viscous, which is not suitable for being prepared as compositions or formulations that can be readily cleaned out of spray equipment. Tribenuron-methyl residues remain in the spray equipment after spraying. Adequate cleanout prior to reuse of the spray equipment will typically require a rinsing procedure that is not only time-consuming but also results in wastewater disposal problems. Therefore, there is a need to provide a novel form of tribenuron-methyl with increased solubility and decreased viscosity. Accordingly, an embodiment of the invention provides a novel crystalline form of tribenuron-methyl, termed "crystalline modification I", and a process for its preparation, as well as agrochemical compositions containing it, and methods for using it in agrochemical applications, such as methods for applying it to plants, plant parts and surroundings. The novel crystalline modification I has been advantageously found to have increased solubility, decreased viscosity, and improved spray equipment clean-out properties.

Accordingly, an embodiment of the invention also provides compositions for controlling the growth of undesirable plants, such as weeds, comprising the crystalline modification I of tribenuron-methyl on its own, as a mixture with auxiliaries and carriers, and as a mixture with other active compounds. The use of the crystalline modification I of tribenuron-methyl in the control of undesired plant growth and a method for the same are also provided by an embodiment of the invention.

BRIEF DESCRIPTION OF DRAWINGS

Various features and aspects of the embodiments of the invention disclosed herein can be more clearly understood by reference to the drawings, which are intended to exemplify and illustrate, but not to limit, the scope of the invention, and wherein.

DETAILED DESCRIPTION OF SPECIFIC EMBODIMENTS

The invention can be more clearly understood by reference to the following detailed description of specific embodiments thereof, which is intended to illustrate, but not limit, the scope of the appended claims.

It has been found that the crystalline modification I of tribenuron-methyl has a significant increase in its solubility and a significant decrease in its viscosity, which significantly reduces the residue contamination and improves spray equipment clean-out properties. In addition, it is found that the crystalline modification I of tribenuron-methyl is easier to comminute or grind compared to amorphous tribenuron-methyl prepared in accordance with the disclosure of EP 0202830. This allows the preparation of commercial formulations such as suspension concentrates (SC), oil-based suspension concentrates (OD), water-dispersible granules (WG) and water-soluble granules (SG). Hence, it is possible to prepare any formulations of tribenuron-methyl in crystalline modification I, which is disclosed hereinafter.

By virtue of its high solubility and low viscosity, the crystalline modification I of tribenuron-methyl is highly suitable for preparing compositions for controlling undesirable weeds.

According to a first aspect of the invention, a crystalline modification I of tribenuron-methyl is provided, exhibiting at least three of the following reflexes, in any combination, as 2θ values in an X-ray powder diffractogram recorded using Cu-Kα radiation at 25° C.:

$$2\theta = 6.47 \pm 0.2 \tag{1}$$

$$2\theta = 10.46 \pm 0.2 \tag{2}$$

$$2\theta = 11.02 \pm 0.2 \tag{3}$$

$$2\theta = 14.01 \pm 0.2 \tag{4}$$

$$2\theta = 15.73 \pm 0.2 \tag{5}$$

$$2\theta = 16.71 \pm 0.2 \tag{6}$$

$$2\theta = 16.98 \pm 0.2 \tag{7}$$

$$2\theta = 21.04 \pm 0.2 \tag{8}$$

$2\theta=22.23\pm0.2$ (9)

$2\theta=23.26\pm0.2$ (10)

$2\theta=25.01\pm0.2$ (11)

$2\theta=26.14\pm0.2$ (12)

Figure 2:
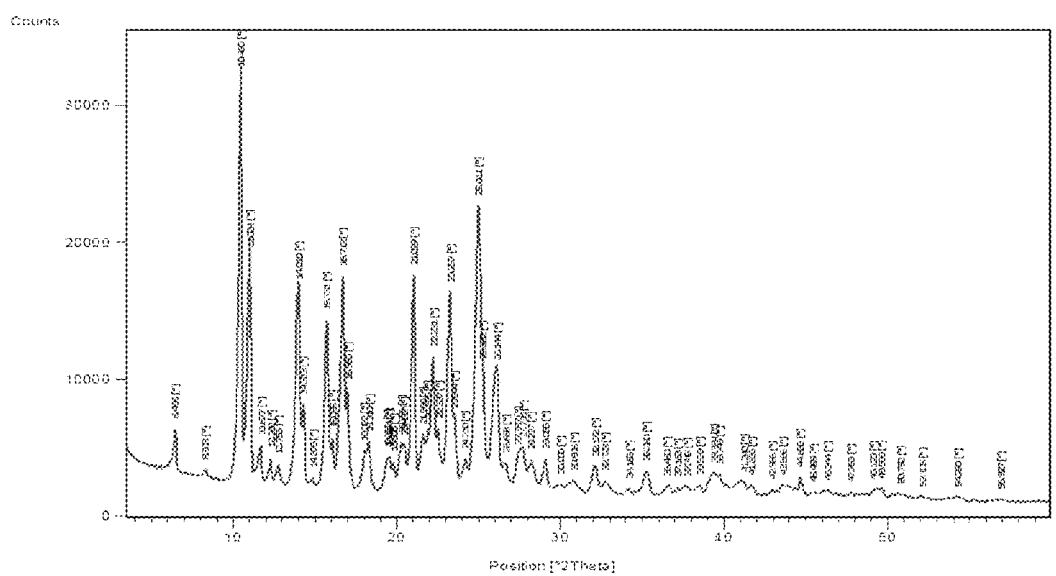
FIG. 2 is a X-ray powder diffractogram of an embodiment of crystalline modification I of tribenuron-methyl.

The crystalline modification I of tribenuron-methyl of an embodiment of the invention is characterized by an X-ray powder diffractogram having at least three of the reflexes indicated above, in any combination thereof. Preferably, the crystalline modification I is one having at least four of the aforementioned reflexes, more preferably at least five six or seven, or eight of said reflexes, again in any combination thereof. An X-ray powder diffractogram of the crystalline modification I of tribenuron-methyl is shown in FIG. 2, which will be described in detail hereinafter.

According to a preferred embodiment the crystalline modification I exhibits at least 3, 4, or 5 or all of the reflexes, in any combination, from the following:

$2\theta=10.46\pm0.2$ (2)

$2\theta=11.02\pm0.2$ (3)

$2\theta=14.01\pm0.2$ (4)

$2\theta=15.73\pm0.2$ (5)

$2\theta=16.71\pm0.2$ (6)

$2\theta=21.04\pm0.2$ (8)

$2\theta=23.26\pm0.2$ (10)

$2\theta=25.01\pm0.2$ (12)

Figure 1:
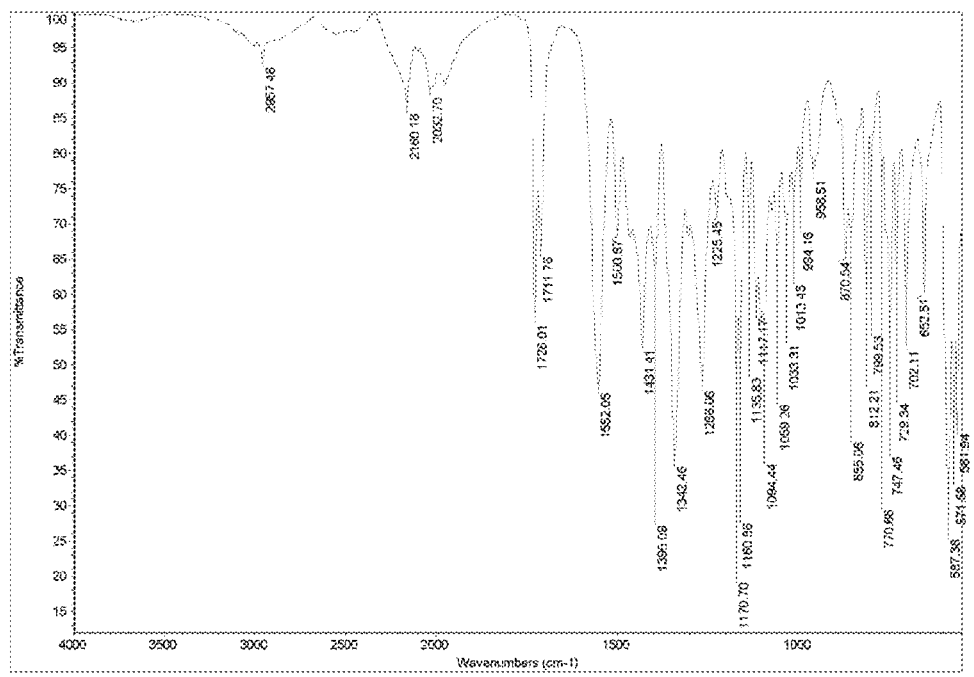
FIG. 1 is an infrared (IR) spectrum of an embodiment of crystalline modification I of tribenuron-methyl.

The X-ray powder diffractogram was taken using a diffractometer from in reflection geometry in the range from 3°-60° with increments of 0.03° using Cu-Ka radiation at 25° C. The crystalline modification I of tribenuron-methyl according to an embodiment of the invention may be further characterized by Infrared (IR) spectroscopy. The IR spectrum was measured with the resolution of 4 cm$^{-1}$ and with the number of scans of 16 for the purified sample. The IR spectrum of crystalline modification I of tribenuron-methyl can be identified by its characteristic functional group vibrations (characteristic bands) at one or more of 2957.46, 2160.18, 2032.70, 1728.01 and 1552.05 cm$^{-1}$ as shown in FIG. 1.

All IR spectra were obtained using the following acquisition parameters:

| | |
|---|---|
| FT-IR spectrometer | Bruker Tensor37 |
| Diamond ATR unit | from Specac |
| Wavelength range | 550-4000 cm$^{-1}$ |
| Resolution | 4 cm$^{-1}$ |
| Number of scans | 16 |

Figure 3:
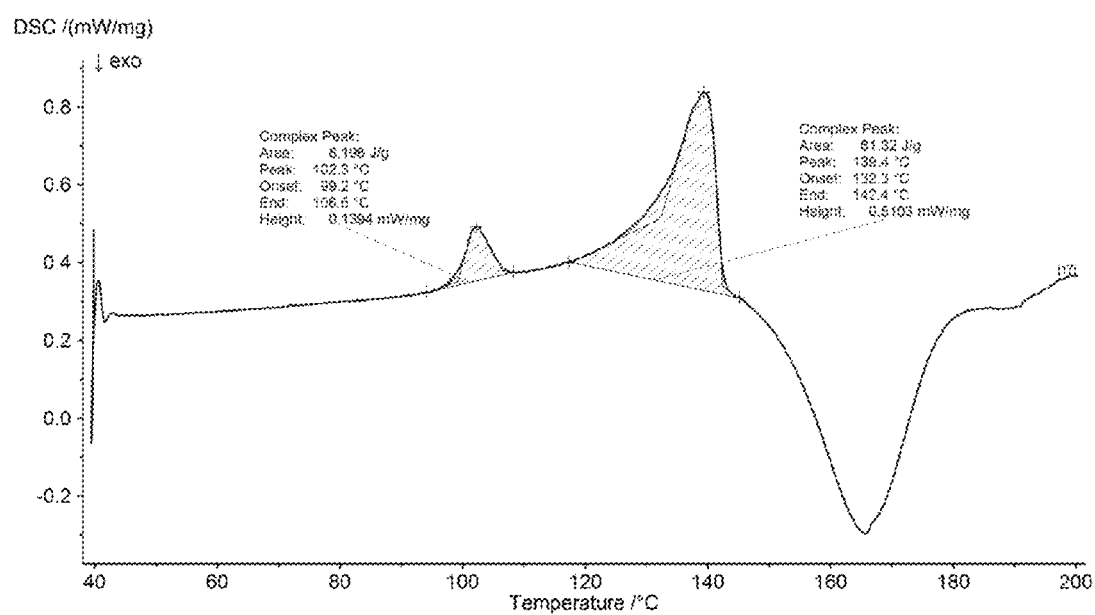
FIG. 3 is a Differential Scanning calorimetry (DSC) thermogram of an embodiment of crystalline modification I of tribenuron-methyl.

The crystalline modification I of tribenuron-methyl according to an embodiment of the invention may be further characterized by Differential Scanning calorimetry (DSC) (FIG. 3). An endothermic melting peak with onset at 132.3° C. and peak maximum at 139.4° C. is shown in FIG. 3.

Methods for preparing amorphous tribenuron-methyl are known in the art. Amorphous tribenuron-methyl is manufactured and available on a commercial scale. A particularly suitable method for preparing amorphous tribenuron-methyl is described in EP 0202830.

According to an embodiment of the invention, the crystalline modification I of tribenuron-methyl can be obtained by the processes below:

Tribenuron-methyl in the amorphous state is dissolved and then crystallized from a solvent.

In one aspect, the present invention provides a process for preparing a crystalline modification I of tribenuron-methyl comprising steps of:
i) dissolving an amorphous tribenuron-methyl in a solvent;
ii) precipitating the dissolved compound into crystalline modification I of tribenuron-methyl of formula I; and
iii) isolating the precipitated crystalline modification I.

Suitable solvents for preparing tribenuron-methyl crystalline modification I include halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions within a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures of these.

Preferred solvents include alcohols aromatic hydrocarbons (such as benzene, toluene, xylene, chlorobenzene), esters and aliphatic alcohols, and mixtures thereof. Particularly preferred solvents or solvent mixtures include isopropanol, toluene, methyl-tetrahydrofuran, diethyl carbonate, chlorobenzene, n-butyl acetate, isobutyl acetate, n-butanol, methanol, ethanol, ethyl malonate, methyl t-butyl ether, and mixtures of toluene and butanol, mixtures of toluene and n-butyl acetate, mixtures of ethyl malonate and methyl t-butyl ether, as well as mixtures of butyl acetate and methyl t-butyl ether. Solvent mixtures of more than 2 or 3 or 4 components are also envisaged by embodiments of the invention.

In an embodiment of the invention, it is preferred that the solvent comprises at least one alcohol, and more preferably comprises at least one straight or branched C1-C8 aliphatic alcohol, more preferably at least one straight or branched C1-C4 aliphatic alcohol, even more preferably at least one of methanol and ethanol.

According to another preferred embodiment, the solvent essentially consists of an alcohol as mentioned above or mixtures thereof.

Hence, according to a preferred embodiment in step (i), amorphous tribenuron-methyl is dissolved in a solvent comprising an alcohol. In a preferred embodiment, the solvent essentially consists of methanol and/or ethanol.

According to a preferred embodiment in step (i), amorphous tribenuron-methyl is dissolved in a solvent or a solvent mixture as a concentrated solution by heating from room temperature or ambient temperature to reflux temperature or below the reflux temperature of the solvent or the solvent mixture. Preferably, the concentrated solutions can be prepared at the reflux temperature of the solvents. The concentration of the solution depends on the solubility of tribenuron-methyl in the corresponding solvent or solvent mixture.

The concentrated homogeneous solution thus prepared as in step (i) is then cooled to room or ambient temperature, or to a temperature of around 0° C. to 20° C. to crystallize the desired crystalline form from the solvent. The crystalline modification I of tribenuron-methyl can also be crystallized out by concentrating the homogeneous solution through removing the solvent or solvent mixture to a certain volume either with or without applying vacuum and cooling to below the reflux temperature of the solvent or the solvent mixture.

Alternatively, or in addition thereto, crystalline modification I of tribenuron-methyl can also be effected by adding seed crystals of the desired crystalline form during crystallization into a solution prepared in step (i), which can promote and/or accelerate the crystallization.

The seed crystal amount added to the concentrated solution is typically in the range of 0.001 to 10% by weight, preferably 0.001 to 2.5 wt %, often 0.005 to 0.5% by weight based on the weight of tribenuron-methyl used for the preparation of concentrated solution in step (i). Preferably, the seed crystals are added to the concentrated solution at the temperature below the boiling point of the corresponding solvent or the solvent mixture.

Hence, the precipitation of the crystalline modification I of tribenuron-methyl can be effectively achieved from the concentrated solution by a person of ordinary skill in the art.

The precipitated crystalline modification I of tribenuron-methyl obtained from step (ii) is isolated by the usual solid component separating techniques from solutions, such as filtration, centrifugation or decantation. Then, the isolated solid precipitate is washed with solvent one or more times. Preferably, the solvent employed in the washing stage consists of one or more components of the solvent or solvent mixture employed for preparation of concentrated solution in step (i), as described hereinbefore. The washing is usually carried out using the corresponding solvent or solvent mixture between room temperature and 0° C., depending on the solubility of the crystal, in order to minimize or avoid the loss of crystalline material in the corresponding washing solvent as much as possible.

The invention, in an embodiment, also relates to a composition comprising the crystalline modification I of tribenuron-methyl. The amount of the crystalline modification I of tribenuron-methyl is less than 75% by weight of the composition, preferably less than 50% by weight of the composition, more preferably less than 30% by weight of the composition, still more preferably about 25% by weight of the composition.

The use of amorphous tribenuron-methyl as a herbicide is known in the art and is used on a commercial scale. The crystalline modification I of tribenuron-methyl is also active in controlling unwanted plant growth, such as weeds. Techniques of formulating and applying amorphous tribenuron-methyl are known in the art, for example as disclosed in the documents described hereinbefore. Tribenuron-methyl in the crystalline modification I of the present invention may be formulated and applied in manner analogous to those described for amorphous tribenuron-methyl.

Accordingly, in a further aspect, an embodiment of the invention provides a herbicidal composition comprising tribenuron-methyl in the crystalline modification I as defined hereinbefore.

Accordingly, an embodiment of the invention furthermore provides processes for preparing compositions for controlling unwanted plant growth using the crystalline modification I of tribenuron-methyl.

Accordingly, the invention also provides a method for controlling unwanted plant growth, comprising applying to the plant, plant part, or surroundings, a herbicidally effective amount of crystalline modification I of tribenuron-methyl.

The crystalline modification I of tribenuron-methyl can be incorporated into the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents, in a manner analogous to that known for amorphous tribenuron-methyl.

In this context, the crystalline modification I of tribenuron-methyl should be present in a concentration of from about 0.1 to about 75% by weight of the total mixture, i.e., in amounts sufficient to achieve the required dosage. The formulations are prepared, for example, by extending the crystalline modification I of tribenuron-methyl with water, solvents and carriers, using, if appropriate, emulsifiers and/or dispersants, and/or other auxiliaries.

These formulations are prepared by mixing the crystalline modification I of tribenuron-methyl with an effective amount of at least one acceptable auxiliaries, for example, surfactants, liquid diluents, solid diluents, wetting agents, dispersants, thickening agent, antifoaming agent and other formulation ingredients.

Liquid diluents include, but are not limited to, water, N,N-dimethylamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetin, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminium, calcium and zinc oxide, and mixtures thereof.

Wetting agents include, but are not limited to, alkyl sulfosuccinates, laureates, alkyl sulfates, phosphate esters, acetylenic diols, ethoxyfluorinated alcohols, ethoxylated silicones, alkyl phenol ethoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures thereof. Alkyl naphthalene sulphonates, sodium salts are particularly useful for the composition of the invention Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates, and mixtures thereof. Ligninsulfonates such as sodium ligninsulfonates are particularly useful for the composition of the invention. Naphthalene sulfonate-formaldehyde condensates such as naphthalenesulfonic acid, polymers with formaldehyde, and sodium salts are particularly useful for the composition of the invention Thickening agents include, but are not limited to, guar gum, pectin, casein, carrageenan, xanthan gum, alginates, methylcellulose, hydroxyethylcellulose, hydroxypropylcellulose and carboxymethylcellulose, and mixtures thereof. Synthetic thickening agents include derivatives of the former categories, and also polyvinyl alcohols, polyacrylamides, polyvinylpyrrolidones, various polyethers, their copolymers as well as polyacrylic acids and their salts, and mixtures thereof. Alkylpolyvinylpyrrolidones are particularly useful for the composition of the invention Other formulation ingredients can also be used in the present invention such as dyes, drying agents, and the like. These ingredients are known to one skilled in the art.

The crystalline modification I of tribenuron-methyl according to an embodiment of the invention can be present in formulations and in its use forms, prepared from these formulations, and as a mixture with one or more other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as a herbicide, the crystalline modification I of tribenuron-methyl according to an embodiment of the invention can furthermore be present in formulations and its use forms, prepared from these formulations, and as a mixture with inhibitors which reduce degradation of the active compounds after their use in the environment of the plant, on the surface of plant parts or in plant tissues.

All plants, plant parts, and their surroundings can be treated in accordance with the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown, the place on which the plant propagation materials of the plants will be sown or the environment near the plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

Treatment according to an embodiment of the invention of the plants, plant parts, and/or their surroundings, with the compositions or formulations of the invention is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the invention are seen most when the herbicidal composition is applied to kill weeds in growing crops of useful plants: such as maize (corn) including field corns, pop corns and sweet corns, cotton, sunflower, cereal, barley, wheat, rice, oats, potatoes, sugar beets, plantation crops (such as bananas, fruit trees, rubber trees, tree nurseries), vines, citrus, olive, amenity, asparagus, bushberries (such as blueberries), caneberries, cranberries, flax, grain sorghum, okra, peppermint, rhubarb, spearmint, turf grass, grapevine and sugarcane. In this invention, treatment of sunflower and cereal are particularly beneficial.

All percentages are given in weight % unless otherwise indicated.

Embodiments of the invention will now be described by way of the following examples, which are provided for illustrative purposes only, and not intended to limit the scope of the disclosure.

EXAMPLES

Example 1

Preparation of Amorphous Tribenuron-Methyl in Accordance with the Disclosure of EP 0202830

To a solution of 2-carbomethoxybenzenesul-fonyl isocyanate (22.4 g 93.0 mmol) in dichloromethane (100 mL) was added 2-methoxy-4-methyl-6-methylamino-1,3,5-triazine (10.7 g, 69.6 mmol), followed by a catalytic amount of 1,4-diaza[2.2.2]bicyclooctane. After stirring overnight at ambient temperature under a nitrogen atmosphere, the reaction mixture was concentrated in vacuo. The residue was triturated with diethyl ether and then washed with 1-chlorobutane to yield the title compound as a white powder (28.8 g).

Scheme 1. Synthesis of Tribenuron-methyl

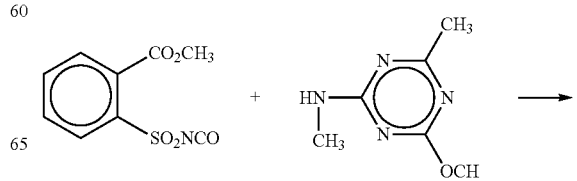

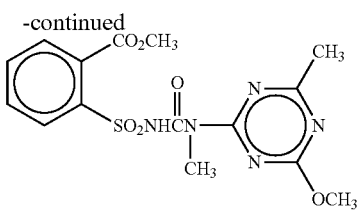

Figure 4:
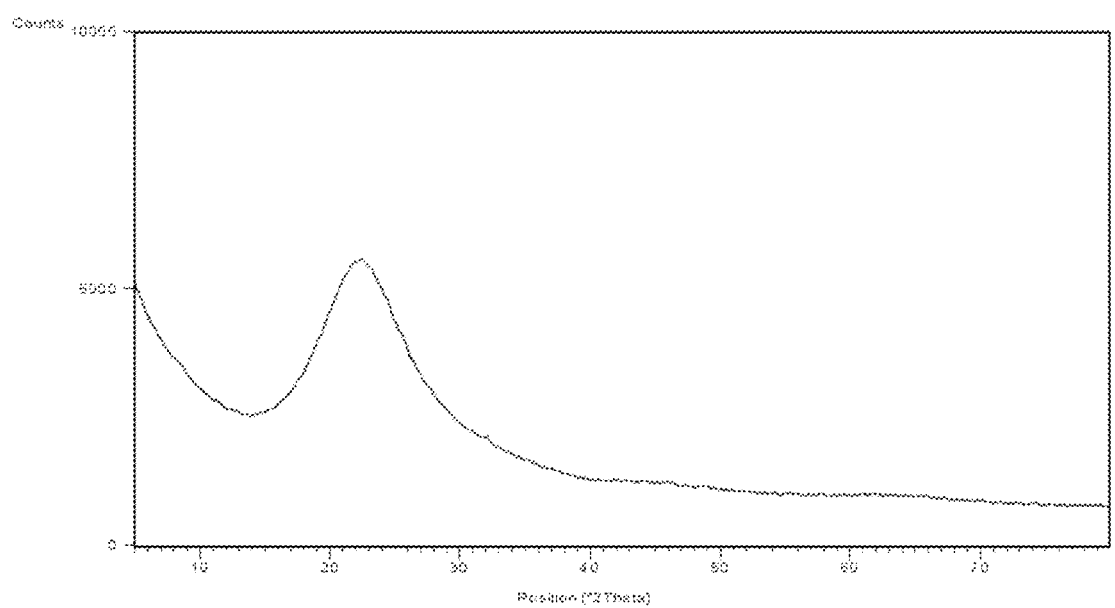
FIG. 4 is a powder X-ray diffractogram of amorphous tribenuron-methyl.

As shown in FIG. 4, the X-ray powder diffraction pattern of the resulting tribenuron-methyl product has no significant individual signals or peaks, which indicates the tribenuron-methyl product prepared in accordance with the disclosure of EP 0202830 A1 is amorphous.

Preparation of Crystalline Modification I of Tribenuron-Methyl

Example 2

Crystallization from Methanol

Tribenuron-methyl sample prepared in Example 1 (10 g) was taken in a three-necked round bottom flask along with methanol (60 mL) and the resulting slurry was heated to 50° C. to get a homogeneous solution. The insoluble particles, if any, were filtered and the solution was slowly cooled to room temperature. Upon cooling, fine crystals were formed and the heterogeneous mixture was stirred at room temperature for 2 hours. Then, the slurry was filtered and washed with methanol (3 mL). The filtered crystals were dried under vacuum in order to remove the methanol traces from the crystalline product. The crystalline product thus obtained had a purity of >98% and was recovered at not less than 80% yield.

The obtained crystal was analyzed by IR, X-ray powder diffraction and DSC, and found to be crystalline modification I of tribenuron-methyl as shown in FIGS. 1, 2 and 3, respectively.

Differential scanning calorimetry (DSC) (FIG. 3) shows an endothermic melting peak with onset at 132.3° C. and peak maximum at 139.4° C. as shown in FIG. 3.

IR spectrum of the crystalline modification I of tribenuron-methyl shows the functional group characteristic vibrations at 2957.46, 2160.18, 2032.70, 1728.01 and 1552.05 cm$^{-1}$ as shown in FIG. 1.

The crystalline modification I of tribenuron-methyl has the X-ray powder diffractogram shown in FIG. 2 with reflexes summarized in Table 1 below. The X-ray powder diffractogram were taken using a diffractometer in reflection geometry in the range from 3°-60° with increments of 0.03° using Cu-Ka radiation at 25° C.

TABLE 1

X-ray powder diffractogram reflexes of crystalline modification I of tribenuron-methyl
Crystal Form A

| 2 θ (°) | d (Å) |
|---|---|
| 6.47 ± 0.2 | 13.67 ± 0.05 |
| 10.46 ± 0.2 | 8.46 ± 0.05 |
| 11.02 ± 0.2 | 8.03 ± 0.05 |
| 14.01 ± 0.2 | 6.32 ± 0.05 |
| 15.73 ± 0.2 | 5.63 ± 0.05 |
| 16.71 ± 0.2 | 5.31 ± 0.05 |
| 16.98 ± 0.2 | 5.22 ± 0.05 |

TABLE 1-continued

X-ray powder diffractogram reflexes of crystalline modification I of tribenuron-methyl
Crystal Form A

| 2 θ (°) | d (Å) |
|---|---|
| 21.04 ± 0.2 | 4.22 ± 0.05 |
| 22.23 ± 0.2 | 4.00 ± 0.05 |
| 23.26 ± 0.2 | 3.82 ± 0.05 |
| 25.01 ± 0.2 | 3.56 ± 0.05 |
| 26.14 ± 0.2 | 3.41 ± 0.05 |

Example 3

Crystallization from Ethanol

Tribenuron-methyl (5 g) sample prepared in Example 1 was taken in a three-necked round bottom flask along with ethanol (35 mL) and the resulting slurry was heated to 60° C. to get a homogeneous solution. The resultant hot solution was filtered to remove the insoluble (if any) and the solution was slowly cooled to ambient temperature. Product was precipitated out as fine crystal during cooling and the mixture was stirred at room temperature for 2 h. Then, the slurry was filtered, washed with ethanol (3 mL). The filtered crystals were dried under vacuum at room temperature in order to remove the ethanol traces from the crystalline product. The crystalline product thus obtained was having a purity of >98% and the recovered yield was found to be not less than 80%.

The crystals were characterized as being tribenuron-methyl crystalline modification I using IR spectrometry, X-ray diffraction and DSC, as described in Example 2.

Example 4

Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Tribenuron-methyl, crystalline modification I, 98% (prepared in Example 2) | 40.8 | 0 | Active compound |
| Amorphous tribenuron-methyl (prepared in Example 1) | 0 | 40.8 | Active compound |
| Modified polyether-polysiloxane | 0.5 | 0.5 | Antifoaming agent |
| Ethoxylated castor oil | 15 | 15 | Emulsifier |
| Sodium alkylnaphthalenesulfonate, formaldehyde | 5 | 5 | Dispersing agent |
| Silica | 2 | 2 | Thickening agent |
| Corn oil | Balance to 100% | Balance to 100% | Carrier |

Example 5

Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Tribenuron-methyl, crystalline modification I, 98% (prepared in Example 2) | 25.51 | 0 | Active compound |
| Amorphous tribenuron-methyl (prepared in Example 1) | 0 | 25.51 | Active compound |
| Lignosulfonic acid, sodium salt, (REAX ® 88B) | 5 | 5 | Antifoaming agent |
| Sodium lauryl sulfate | 0.5 | 0.5 | Wetting agent |
| Sodium hydrogen carbonate | 2 | 2 | Filler |
| Potassium sulfate | Balance to 100% | Balance to 100% | carrier |

Example 6

Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Tribenuron-methyl, crystalline modification I, 98% (prepared in Example 2) | 25.51 | 0 | Active compound |
| Amorphous tribenuron-methyl (prepared in Example 1) | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B | 15 | 15 | Dispersing agent |
| Naphthalenesulfonic acid, polymer with formaldehyde, sodium salt (TAMOL ® NN8906) | 6 | 6 | Dispersing agent |
| Non-ionic aqueous emulsion of polydimethylsiloxanes | 1 | 1 | Antifoaming agent |
| Mannitol | Balance to 100% | Balance to 100% | Carrier |

Example 7

Determining Water Solubility

A stock pH 7 buffer solution was prepared by adding aqueous sodium hydroxide solution (0.1 M, 145 mL) to aqueous potassium dihydrogen phosphate solution (0.1 M, 250 mL), and then adding sufficient distilled water to adjust the final volume to 500 mL. At least 1 time and up to about 5 times the amount of tribenuron-methyl needed for saturation was added to a mixing vessel containing stock buffer solution at the test temperature (e.g., 20° C.). The mixture was magnetically stirred in the dark while being maintained at the test temperature. Samples were periodically removed for analysis. The samples were centrifuged using a high speed, temperature-controlled centrifuge at the test temperature for about 20 minutes at >12000 G to remove suspended particles. An aliquot of each supernatant was taken for analysis.

The concentration of tribenuron-methyl in the supernatant was determined by a high pressure liquid chromatography (HPLC) with a reversed phase chromatography column and UV detection. The method should include development of best-fit calibration curves based on at least three standards using linear regression analysis. Samples were successively withdrawn from the mixing vessel and analyzed until three successive samples show little or no variation in concentration. The test is preferably replicated to ensure accuracy.

TABLE 5

| Sample | Formulation | Original concentration, % | Concentration measured by HPLC after treatment, % | Solubility |
|---|---|---|---|---|
| Tribenuron-methyl, crystalline modification I, 98% (prepared in Example 2) | OD | 40 | 35 | 88% |
| Amorphous tribenuron-methyl (prepared in Example 1) | OD | 40 | 14 | 35% |
| Tribenuron-methyl, crystalline modification I, 98% (prepared in Example 2) | SG | 25 | 24.9 | 99.6% |
| Amorphous tribenuron-methyl (prepared in Example 1) | SG | 25 | 15 | 60% |
| Tribenuron-methyl, crystalline modification I, 98% (prepared in Example 2) | WG | 25 | 23 | 92% |
| Amorphous tribenuron-methyl (prepared in Example 1) | WG | 25 | 12 | 48% |

Example 8

Cleanout Test

The cleanout test was conducted by dispersing in water a sample to produce a concentration that is normally used when applying the herbicide: 25% tribenuron-methyl. The sample was added to tap water (300 mL) in a 400 mL beaker and magnetically stirred for 2 minutes. The mixture was then stirred for 2 minutes, whereupon the resulting dispersion was dispensed in three 100 mL aliquots to 4-oz (118 mL) polyethylene bottles. The bottles were capped, inverted twice and allowed to stand overnight.

After standing overnight, each individual bottle was inverted twice and the liquid contents were then poured out. Tap water (10 mL) was added and the bottle was inverted until all sediment was re-suspended, whereupon the contents were poured out. Tap water (100 mL) was added and the bottle was inverted twice and then allowed to stand undisturbed for 10 minutes. The bottle was inverted twice more and the contents were poured out. Acetonitrile (10 mL) was added to the bottle to extract any remaining material. The acetonitrile solution was analyzed by reversed-phase liquid chromatography with UV detection. The cleanout rating (the concentration of tribenuron-methyl herbicide in the acetonitrile solution) is reported in % in Table 6 below. Lower cleanout ratings indicate more effective cleanout compared to higher ratings.

TABLE 6

| Sample | Formulation | Cleanout rating, % |
|---|---|---|
| Tribenuron-methyl, crystalline modification I, 98% (prepared in Example 2) | OD | 5 |
| Amorphous tribenuron-methyl, prepared in Example 1 | OD | 26 |
| Tribenuron-methyl, crystalline modification I, 98% (prepared in Example 2) | SG | 0.1 |
| Amorphous tribenuron-methyl, prepared in Example 1 | SG | 10 |
| Tribenuron-methyl, crystalline modification I, 98% (prepared in Example 2) | WG | 2 |
| Amorphous tribenuron-methyl (prepared in Example 1) | WG | 13 |

The results in Table 6 demonstrate that the crystalline modification I of tribenuron-methyl exhibited markedly superior cleanout properties to those of the known amorphous tribenuron-methyl product.

The invention claimed is:

1. A crystalline modification I of (methyl 2-[4-methoxy-6-methyl-1,3,5-triazin-2-yl(methyl)carbamoylsulfamoyl] benzoate) (Tribenuron-methyl) exhibiting each of the following reflexes as 2θ values in X-ray powder diffractogram recorded using Cu-Kα radiation at 25° C.:

$$2\theta=6.47\pm0.2 \quad (1)$$

$$2\theta=10.46\pm0.2 \quad (2)$$

$$2\theta=11.02\pm0.2 \quad (3)$$

$$2\theta=14.01\pm0.2 \quad (4)$$

$$2\theta=15.73\pm0.2 \quad (5)$$

$$2\theta=16.71\pm0.2 \quad (6)$$

$$2\theta=16.98\pm0.2 \quad (7)$$

$$2\theta=21.04\pm0.2 \quad (8)$$

$$2\theta=22.23\pm0.2 \quad (9)$$

$$2\theta=23.26\pm0.2 \quad (10)$$

$$2\theta=25.01\pm0.2 \quad (11)$$

$$2\theta=26.14\pm0.2 \quad (12).$$

2. The crystalline modification I of tribenuron-methyl according to claim 1, exhibiting an IR spectrum with the characteristic bands at one or more of 2957.46, 2160.18, 2032.70, 1728.01, and 1552.05 $cm^{-1}$.

3. The crystalline modification I of tribenuron-methyl according to claim 1, exhibiting a Differential Scanning calorimeter (DSC) thermogram having an endothermic melting peak with onset at 132.3° C. and peak maximum at 139.4° C.

4. A process of preparing the crystalline modification I of tribenuron-methyl according to claim 1, comprising:
   i) dissolving an amorphous tribenuron-methyl into a solvent;
   ii) precipitating the dissolved compound into the crystalline modification I of tribenuron-methyl; and
   iii) isolating the precipitated crystalline modification I.

5. The process according to claim 4, wherein the solvent is methanol, ethanol, or a mixture thereof.

6. The process according to claim 4, wherein step ii) comprises concentrating the solvent, or cooling the dissolved compound and solvent to ambient temperature, or to a temperature of around 0° C. to 20° C., or adding seed crystals of the crystalline modification I, or a combination of these.

7. A crystalline modification I of tribenuron-methyl obtained according to the process of claim 4, and wherein crystalline modification I of tribenuron-methyl has a purity of at least 98% by weight.

8. A composition comprising an herbicidally effective amount of the crystalline modification I of tribenuron-methyl according to claim 1, and at least one herbicidally acceptable auxiliary.

9. The composition according to claim 8, wherein the auxiliary is selected from the group consisting of one or more of a surfactant, a diluent, a wetting agent, a dispersant, a thickening agent and an antifoaming agent.

10. The composition according to claim 8, wherein the crystalline modification I of tribenuron-methyl is incorporated into the form of a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) or a water-dispersible granule (WG).

11. The composition according to claim 10, wherein the crystalline modification I of tribenuron-methyl is incorporated into the form of an oil-based suspension concentrate (OD), a water-dispersible granule (WG) or a water-soluble granule (SG).

12. A method for controlling unwanted plant growth, comprising applying to the plant, plant part, or surroundings of the plant, a herbicidally effective amount of crystalline modification I of tribenuron-methyl according to claim 1.

* * * * *